(12) United States Patent
Sheridan et al.

(10) Patent No.: US 12,727,954 B2
(45) Date of Patent: Sep. 8, 2026

(54) SURGICAL TOOLS WITH END EFFECTOR REDIRECT PULLEYS

(71) Applicant: CILAG GMBH INTERNATIONAL, Zug (CH)

(72) Inventors: Mark Sheridan, Cincinnati, OH (US); Troy Richardson, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 355 days.

(21) Appl. No.: 18/356,061

(22) Filed: Jul. 20, 2023

(65) Prior Publication Data

US 2025/0025252 A1 Jan. 23, 2025

(51) Int. Cl.
*A61B 34/00* (2016.01)
*A61B 34/37* (2016.01)

(52) U.S. Cl.
CPC .............. *A61B 34/71* (2016.02); *A61B 34/37* (2016.02)

(58) Field of Classification Search
CPC .... A61B 2034/305; A61B 34/37; A61B 34/71
See application file for complete search history.

(56) References Cited

U.S. PATENT DOCUMENTS

2018/0153627 A1* 6/2018 Remm .................. A61B 34/71
2020/0405424 A1* 12/2020 Schuh .................. A61B 34/71

* cited by examiner

*Primary Examiner* — Scott Luan
(74) *Attorney, Agent, or Firm* — Vorys, Sater, Seymour and Pease LLP

(57) ABSTRACT

A surgical tool includes a shaft extending from a drive housing, an end effector including opposing jaws, and a wrist interposing the shaft and the end effector and including a distal clevis to which the jaws are rotatably mounted at a first axle, a proximal clevis rotatably mounted to the distal clevis at a second axle and operatively coupled to the shaft, a set of pulleys rotatably mounted to the second axle, and first and second redirect pulleys rotatably mounted to the distal clevis and axially interposing the pulleys and the jaws. A first closure cable extends through the pulleys to the first redirect pulley, which redirects the first closure cable with no fleet angle to the first jaw, and a second closure cable extends through the pulleys to the second redirect pulley, which redirects the second closure cable with no fleet angle to the second jaw.

19 Claims, 6 Drawing Sheets

SURGICAL TOOLS WITH END EFFECTOR REDIRECT PULLEYS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

In cable-driven MIS instruments, wrist architecture is vital in helping to reduce cable tension while enhancing mechanical advantage. Wrist architecture can also be a source of high strain if small pulleys with large fleet angles are incorporated. Improved wrist architecture is always desirable to reduce costs and improve tool useful life.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure generally describes robotic surgical tools and, more specifically, surgical tool end effectors with redirect pulleys configured to mitigate or eliminate fleet angle.

The embodiments disclosed herein describe a surgical tool that includes a shaft extending from a drive housing, an end effector including opposing jaws, and a wrist interposing the shaft and the end effector and including a distal clevis to which the jaws are rotatably mounted, a proximal clevis rotatably mounted to the distal clevis and operatively coupled to the shaft, a set of pulleys rotatably mounted to the second axle, and first and second redirect pulleys rotatably mounted to the distal clevis and axially interposing the pulleys and the jaws. A first closure cable extends through the pulleys to the first redirect pulley, which redirects the first closure cable with no fleet angle to the first jaw, and a second closure cable extends through the pulleys to the second redirect pulley, which redirects the second closure cable with no fleet angle to the second jaw.

Figure 1:
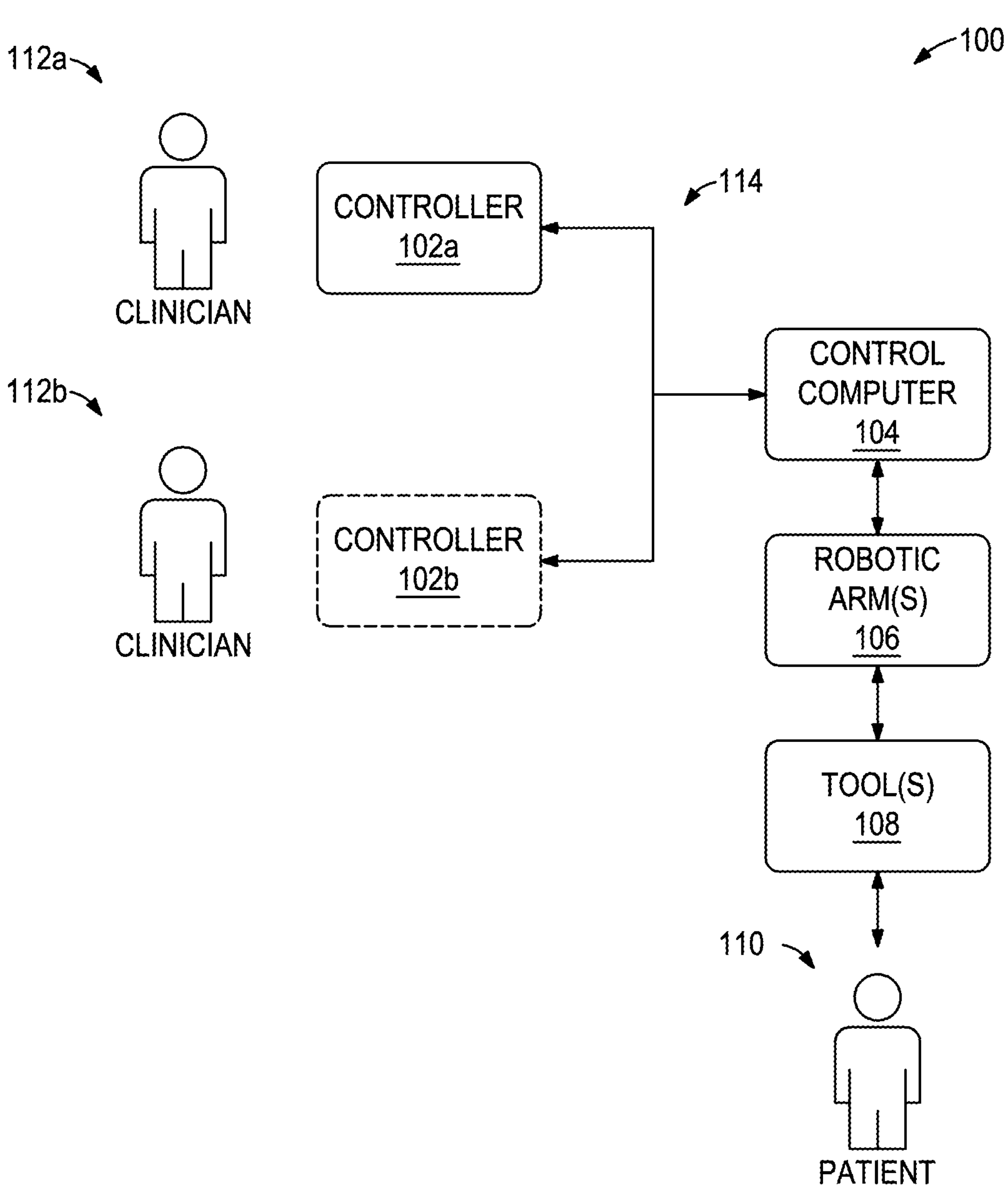
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
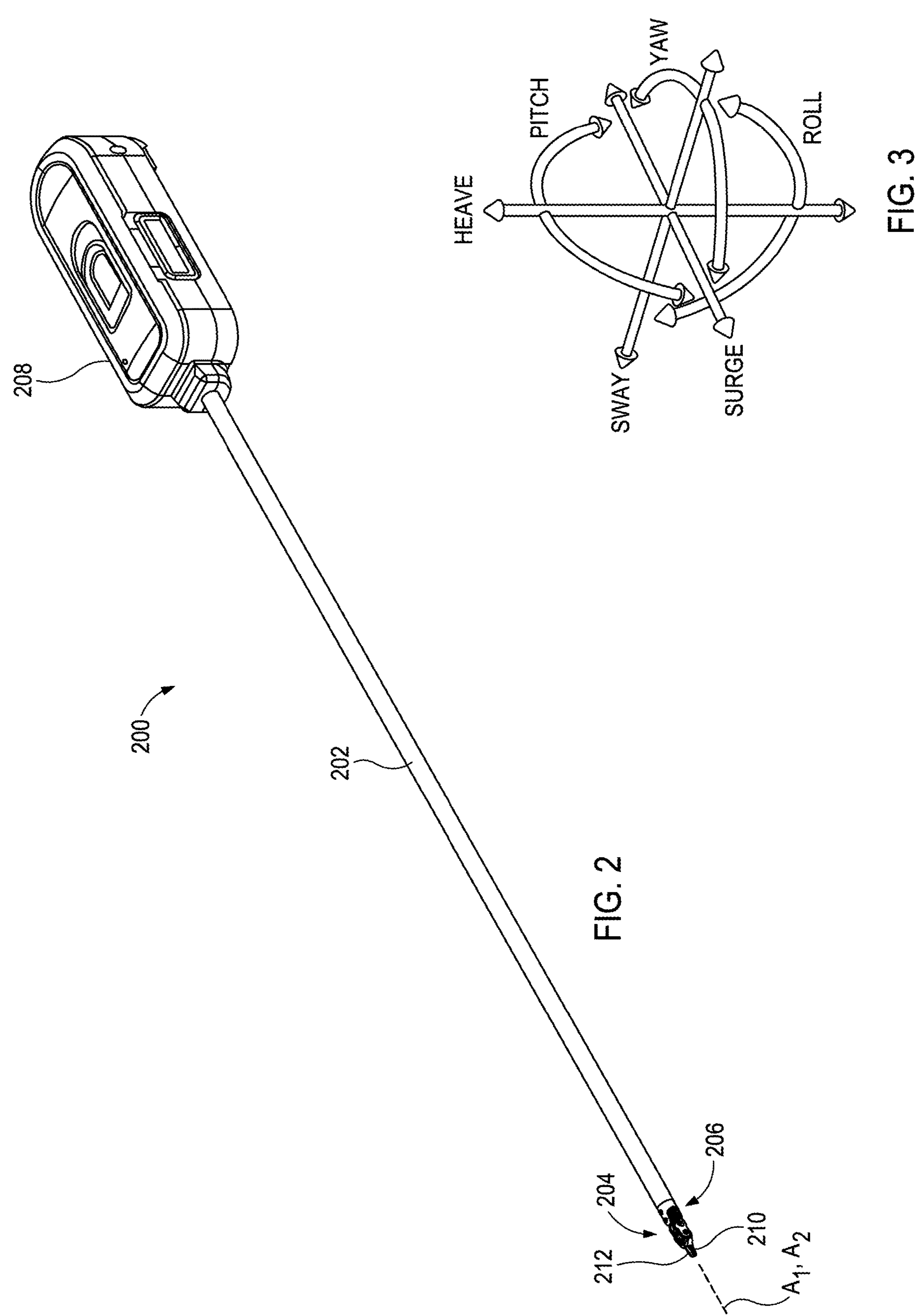
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the drive housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the drive housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the drive housing 208 is configured to control rotational movement of the shaft 202 about the longitudinal axis $A_1$.

The shaft 202 is an elongate member extending distally from the drive housing 208 and has at least one lumen extending therethrough along its axial length. In some embodiments, the shaft 202 may be fixed to the drive housing 208, but could alternatively be rotatably mounted to the drive housing 208 to allow the shaft 202 to rotate about the longitudinal axis $A_1$. In yet other embodiments, the shaft 202 may be releasably coupled to the drive housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper or "needle driver" that includes opposing first (upper) and second (lower) jaws 210, 212 configured to move (articulate) between open and closed positions. As will be appreciated, however, the opposing jaws 210, 212 may alternatively form part of other types of end effectors such as, but not limited to, surgical scissors, a clip applier, a babcock including a pair of opposed grasping jaws, bipolar jaws (e.g., bipolar Maryland grasper, forceps, a fenestrated grasper, etc.), etc. One or both of the jaws 210, 212 may be configured to pivot to transition the end effector 204 between the open and closed positions.

FIG. 3 illustrates the potential degrees of freedom in which the wrist 206 may be able to articulate (pivot) and thereby correspondingly move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Selectively actuating the drive cables, for example, can cause the jaws 210, 212 to move (transition) between open and closed positions. Moreover, selectively actuating the drive cables can also cause the end effector 204 to articulate (move) between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Figure 4A:
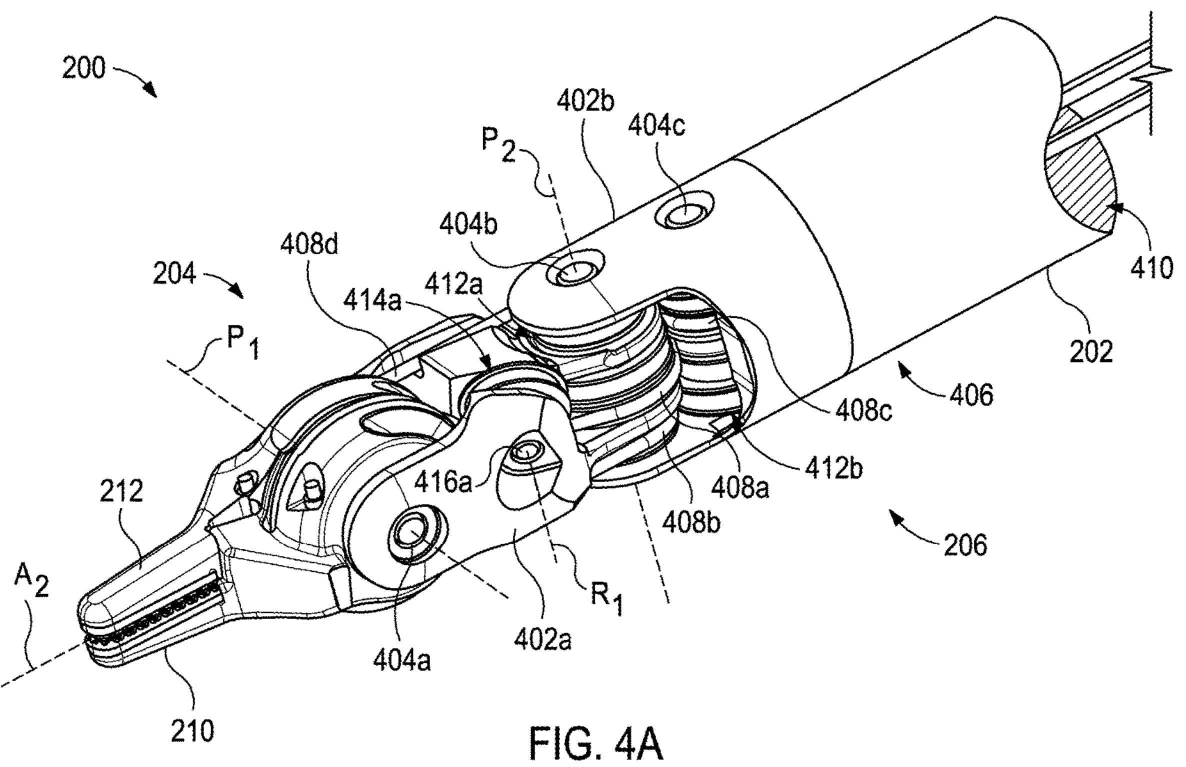
FIGS. 4A and 4B are enlarged isometric views of the distal end of the surgical tool of FIG. 2 from opposing vantage points, according to one or more embodiments.
Figure 4B:
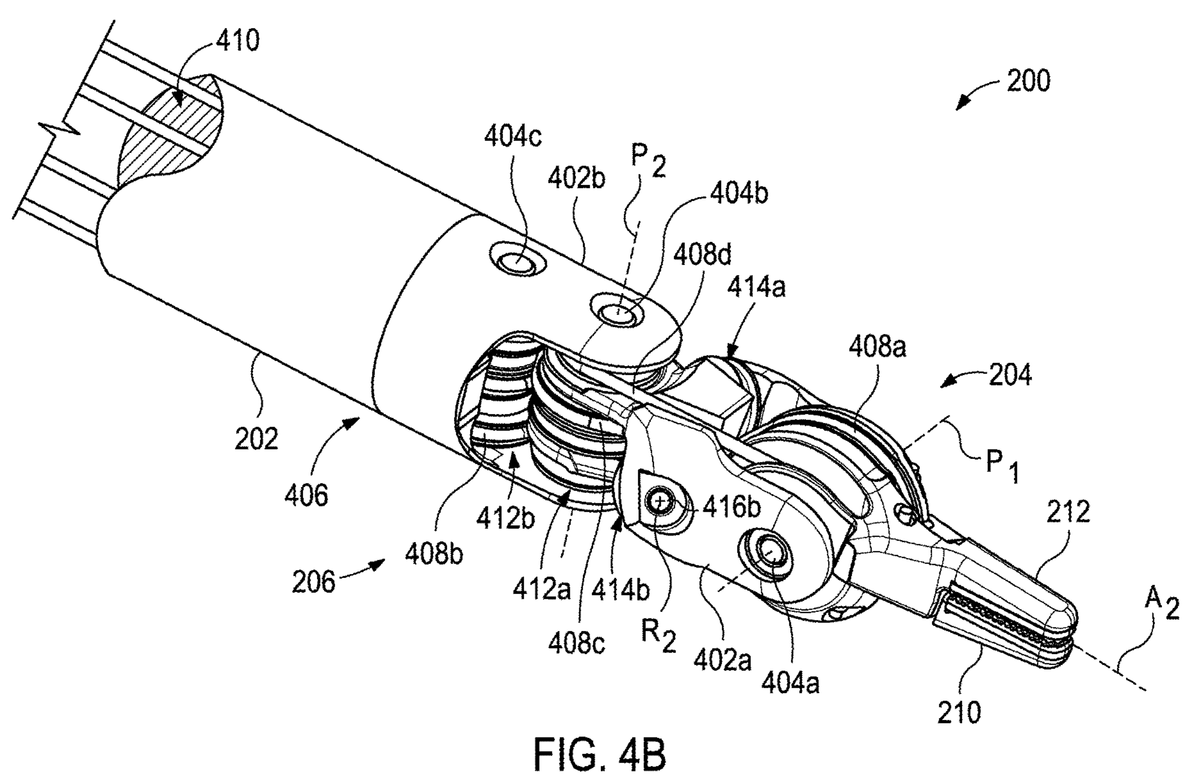

FIGS. 4A and 4B are enlarged, isometric views of the distal end of the surgical tool 200, according to one or more embodiments. More specifically, FIG. 4A is an enlarged, isometric view of the end effector 204 and the wrist 206 from a right side perspective, and FIG. 4B is an enlarged, isometric view of the end effector 204 and the wrist 206 from a left side perspective. The wrist 206 operatively couples the end effector 204 to the shaft 202 (or a shaft adapter interposing the distal end of the shaft 202 and the wrist 206). To accomplish this, the wrist 206 includes a distal clevis 402*a* and a proximal clevis 402*b*. The jaws 210, 212 are rotatably mounted to the distal clevis 402*a* at a first axle 404*a*, the distal clevis 402*a* is rotatably mounted to the proximal clevis 402*b* at a second axle 404*b*, and the proximal clevis 402*b* is operatively coupled to a distal end 406 of the shaft 202.

The wrist 206 provides a first pivot axis $P_1$ that extends through the first axle 404*a* and a second pivot axis $P_2$ that extends through the second axle 404*b*. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "pitch" (up and down) articulation of the end effector 204, and movement about the second pivot axis $P_2$ provides "yaw" (left and right) articulation of the end effector 204. The jaws 210, 212 are mounted at the first pivot axis $P_1$, which allows the jaws 210, 212 to pivot relative to each other to open and close the end effector 204 or alternatively pivot in tandem to articulate the orientation of the end effector 204.

A plurality of drive cables, shown as drive cables 408*a*, 408*b*, 408*c*, and 408*d*, extend longitudinally within a lumen 410 defined by the shaft 202 and pass through the wrist 206 to be operatively coupled to the end effector 204. The lumen 410 can be a single lumen, as illustrated, or can alternatively comprise a plurality of independent lumens, where each lumen receives one or more of the drive cables 408*a-d*.

The drive cables 408*a-d* may form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 408*a-d* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 408*a-d* are depicted in FIGS. 4A-4B, more or less than four may be employed, without departing from the scope of the disclosure.

The drive cables 408*a-d* extend proximally from the end effector 204 to the drive housing 208 (FIG. 2) where they are operatively coupled to various actuation mechanisms or devices housed (contained) therein to facilitate longitudinal movement (translation) of the drive cables 408*a-d* within the lumen 410. Selective actuation of one or all of the drive cables 408*a-d* causes the end effector 204 to articulate (pivot) relative to the shaft 202. More specifically, selective actuation causes a corresponding drive cable 408*a-d* to translate longitudinally within the lumen 410 and thereby causes articulating or operating movement of the end effector 204. One or more drive cables 408*a-d*, for example, may be actuated to cause the end effector 204 to articulate (e.g., both of the jaws 210, 212 moved in a same direction), to cause the end effector 204 to open (e.g., one or both of the jaws 210, 212 move away from the other), or to cause the end effector 204 to close (e.g., one or both of the jaws 210, 212 move toward the other).

Moving the drive cables 408*a-d* can be accomplished in a variety of ways, such as by triggering an associated actuator or mechanism operatively coupled to or housed within the drive housing 208 (FIG. 2). Moving a given drive cable 408*a-d* constitutes applying tension (i.e., pull force) to the given drive cable 408*a-d* in a proximal direction, which causes the given drive cable 408*a-d* to translate and thereby cause the end effector 204 to move (articulate) relative to the shaft 202.

The wrist 206 includes a first set of pulleys 412*a* and a second set of pulleys 412*b*, each configured to interact with and redirect the drive cables 408*a-d* as they pass through the wrist 206 to be operatively coupled to the end effector 204. The first set of pulleys 412*a* is rotatably mounted to the proximal clevis 402*b* at the second axle 404*b* and the second set of pulleys 412*b* is also rotatably mounted to the proximal clevis 402*b* but at a third axle 404*c* located proximal to the second axle 404*b*. The first and second sets of pulleys 412*a,b* cooperatively redirect the drive cables 408*a-d* through an "S" shaped pathway (alternately referred to as an "S-curve" or "S-bend") before being operatively coupled to the end effector 204 at the jaws 210, 212. The drive cables 408*a-d* may be operatively coupled to the jaws 210, 212 via a variety of ways such as, but not limited to, crimps, welds, mechanical fasteners, or any combination thereof.

In at least one embodiment, one pair of drive cables 408*a-d* is operatively coupled to each jaw 210, 212 and configured to "antagonistically" operate the corresponding jaw 210, 212. In the illustrated embodiment, for example, the first and second drive cables 408*a,b* are coupled to (terminate at) the first jaw 210, and the third and fourth drive cables 408*c,d* are coupled to (terminate at) the second jaw 212. Actuation of the first drive cable 408*a* acts on and pivots the first jaw 210 about the first pivot axis $P_1$ toward the closed position. In contrast, actuation of the second drive cable 408*b* acts on and pivots the first jaw 210 about the first pivot axis $P_1$ toward the open position. Similarly, actuation of the third drive cable 408*c* pivots the second jaw 212 about the first pivot axis $P_1$ toward the closed position, while actuation of the fourth drive cable 408*d* pivots the second jaw 212 about the first pivot axis $P_1$ toward the open position. Accordingly, the first and third drive cables 408*a,c* may alternatively be referred to herein as "closure" cables, and the second and fourth drive cables 408*b,c* may alternatively be referred to herein as "open" cables. Simultaneous actuation of the closure cables 408*a,c* will cause the jaws 210, 212 to close, and simultaneous actuation of the open cables 408*b,d* will cause the jaws 210, 212 to open.

The drive cables 408*a-d* may be characterized or otherwise referred to as "antagonistic" cables that cooperatively (yet antagonistically) operate to cause relative or tandem movement of the first and second jaws 210, 212. More particularly, when the first drive cable 408*a* is actuated (moved), the second drive cable 408*b* naturally follows since it is also coupled to the first jaw 210, and vice versa. Similarly, when the third drive cable 408*c* is actuated, the fourth drive cable 408*d* naturally follows since it is also coupled to the second jaw 210, and vice versa.

Accordingly, coordinated actuation of the open and closure cables 408*a-d* may cause the jaws 210, 212 to open or close, and also articulate the end effector 204 about one or both of the first and second pivot axes $P_1$, $P_2$. Consequently, the end effector 204 can articulate with multiple degrees of freedom, e.g., a degree of freedom by articulating about the first pivot axis $P_1$ and another degree of freedom by articulating about the second pivot axis $P_2$. The wrist 206 in this embodiment is pivotable about the second pivot axis $P_2$ in a single plane, e.g., in one of pitch and yaw, and the end effector 204 is pivotable about the first pivot axis $P_1$ in a single, different plane, e.g., the other of pitch and yaw.

According to embodiments of the present disclosure, the wrist 206 may further include a first redirect pulley 414*a* and a second redirect pulley 414*b*. The redirect pulleys 414*a,b* may be rotatably mounted to the distal clevis 402*a* and arranged to axially interpose the first set of pulleys 412*a* and the jaws 210, 212. The first redirect pulley 414*a* may be configured to receive the first drive cable 408*a* (i.e., the "first closure cable") from the first set of pulleys 412*a* and redirect the first closure cable 408*a* to the first jaw 210. Similarly, the second redirect pulley 414 may be configured to receive the third drive cable 408*c* (i.e., the "second closure cable") from the first set of pulleys 412*a* and redirect the second closure cable 408*c* to the second jaw 212. As described in more detail below, redirecting the first and second closure cables 408*a,c* from the first set of pulleys 412*a* to the jaws 210, 212 using the redirect pulleys 414*a,b* may help reduce or entirely eliminate the fleet angle of the first and second closure cables 408*a,c* as they are received by the first and second jaws 210, 212, respectively.

As illustrated, the first redirect pulley 414*a* is rotatably mounted to the distal clevis 402*a* at a first redirect axle 416*a* (FIG. 4A), and the second redirect pulley 414*b* is rotatably mounted to the distal clevis 402*a* at a second redirect axle 416*b* (FIG. 4B). Moreover, the first redirect pulley 414*a* is rotatable about a first redirect axis $R_1$ (FIG. 4A), and the second redirect pulley 414*b* is rotatable about a second redirect axis $R_2$ (FIG. 4B). The first and second redirect axes $R_1$, $R_2$ are angularly offset from each of the longitudinal axis $A_2$ of the end effector 204, the first pivot axis $P_1$, and the second pivot axis $P_2$. In some embodiments, for example, the first and second redirect axes $R_1$, $R_2$ may be angularly offset from the first pivot axis $P_1$ by around 45° and simultaneously angularly offset from the second pivot axis $P_2$ by around 45°. In other embodiments, however, the first and second redirect axes $R_1$, $R_2$ may be angularly offset from the first and second pivot axes $P_1$, $P_2$ by more or less than 45°, without departing from the scope of the disclosure.

Figures 7A, 7B, 7C:
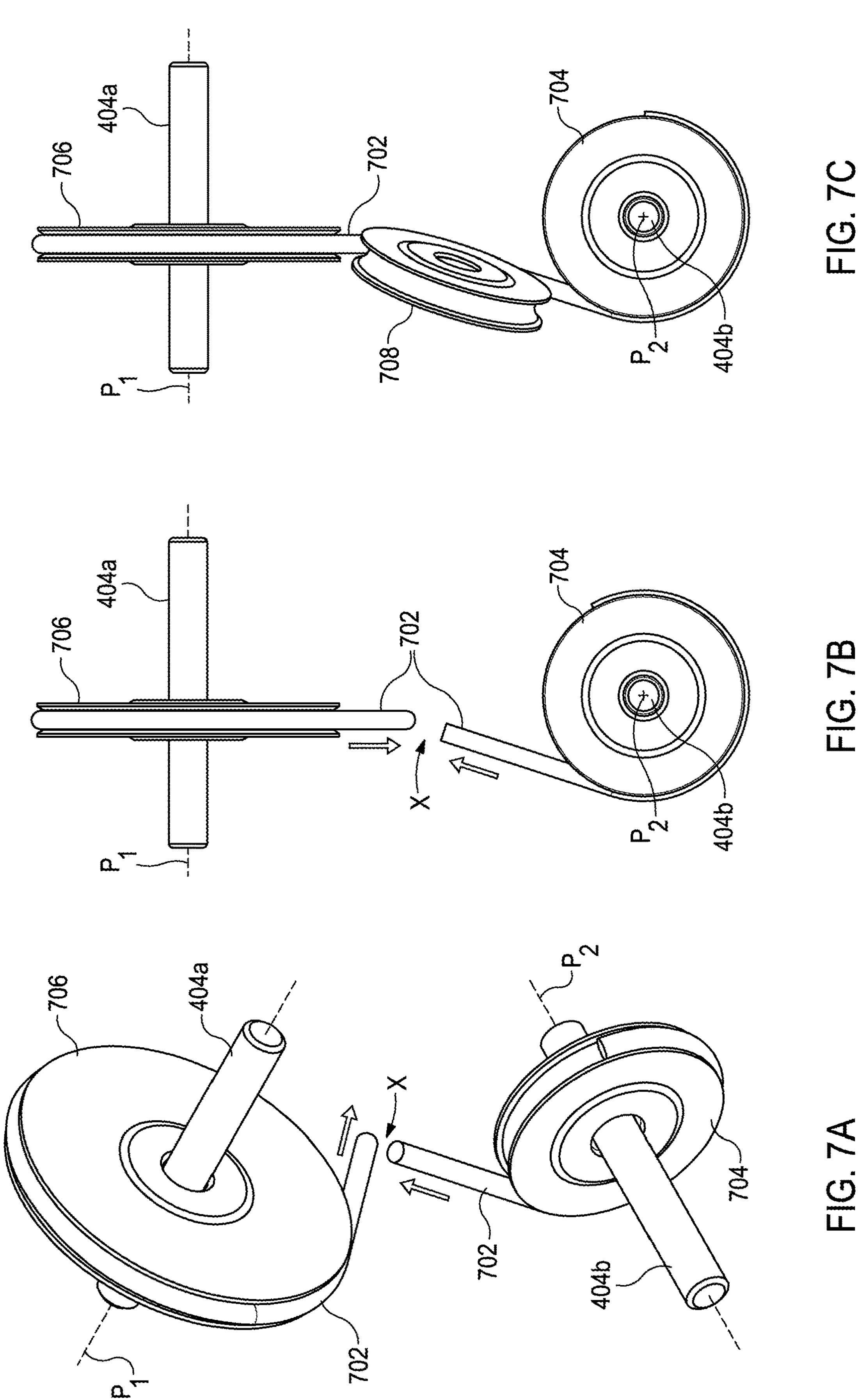
FIGS. 7A-7C graphically depict the inclusion of a redirect pulley between yaw and pitch pulleys to eliminate fleet angle, according to embodiments of the present disclosure.

In at least one embodiment, the redirect pulleys 414*a,b* are mounted to the distal clevis 402*a* such that each redirect pulley 414*a,b* exhibits a diametral tangent to both the first set of pulleys 412*a* and the corresponding jaw 210, 212, which helps reduce or entirely eliminate the fleet angle of the first and second closure cables 408*a,c* as they are received by the first and second jaws 210, 212, respectively. More specifically, the first redirect pulley 414*a* receives the first closure cable 408*a* at a first tangent vector ("TAN 1") extending to the first set of pulleys 412*a*, and conveys the first closure cable 408*a* at a second tangent vector ("TAN 2") to the first jaw 210, where TAN 1 and TAN 2 intersect at a common point about the circumference of the first redirect pulley 414*a*. Moreover, the first redirect axis $R_1$ is perpendicular to TAN 1 and TAN 2 and places the first redirect pulley 414*a* tangent to TAN 1 and TAN 2. Similarly, the second redirect pulley 414*a* receives the second closure cable 408*b* at a third tangent vector ("TAN 3") extending to the first set of pulleys 412*a*, and conveys the second closure cable 408*b* at a fourth tangent vector ("TAN 4") to the second jaw 212, where TAN 3 and TAN 4 intersect at a common point about the circumference of the second redirect pulley 414*b*. Moreover, the second redirect axis $R_2$ is perpendicular to TAN 3 and TAN 4 and places the second redirect pulley 414*b* tangent to TAN 3 and TAN 4. The foregoing description is graphically supported in more detail below with reference to FIGS. 7A-7C.

Figure 5A:
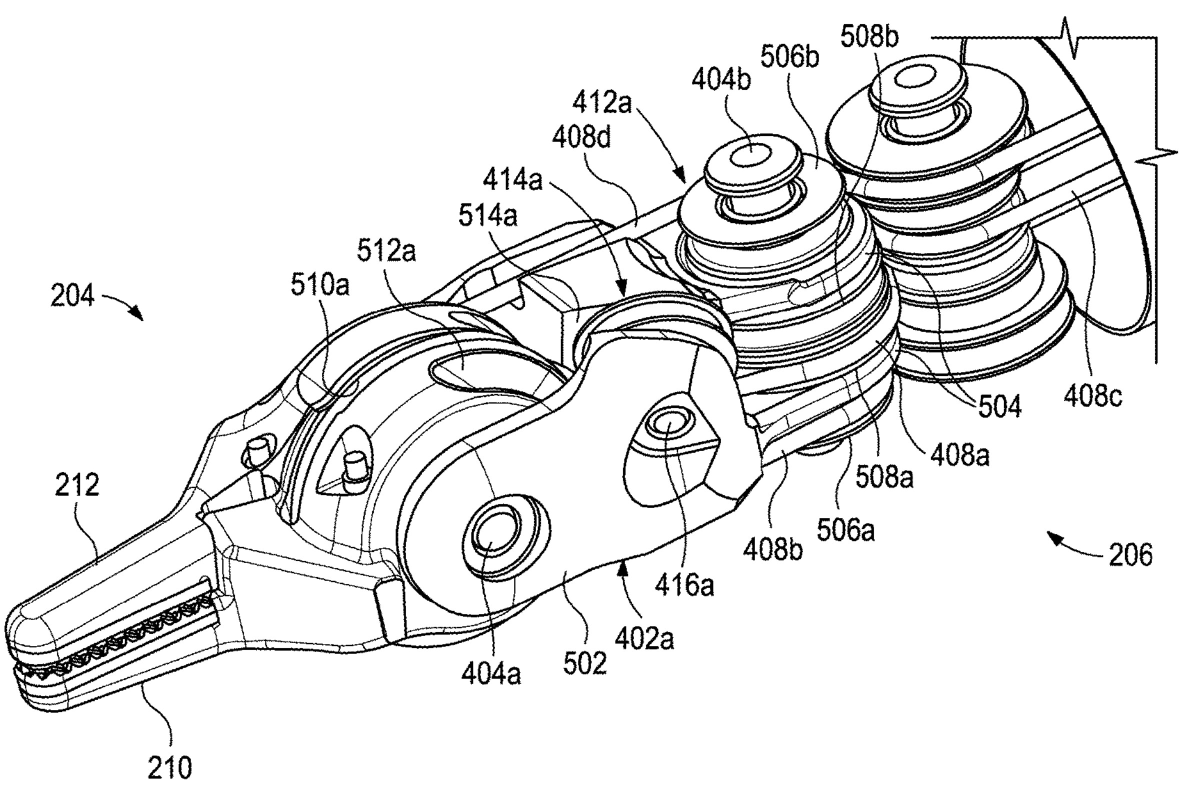
FIGS. 5A and 5B are enlarged isometric views of the end effector and the wrist, according to one or more embodiments.
Figure 5B:
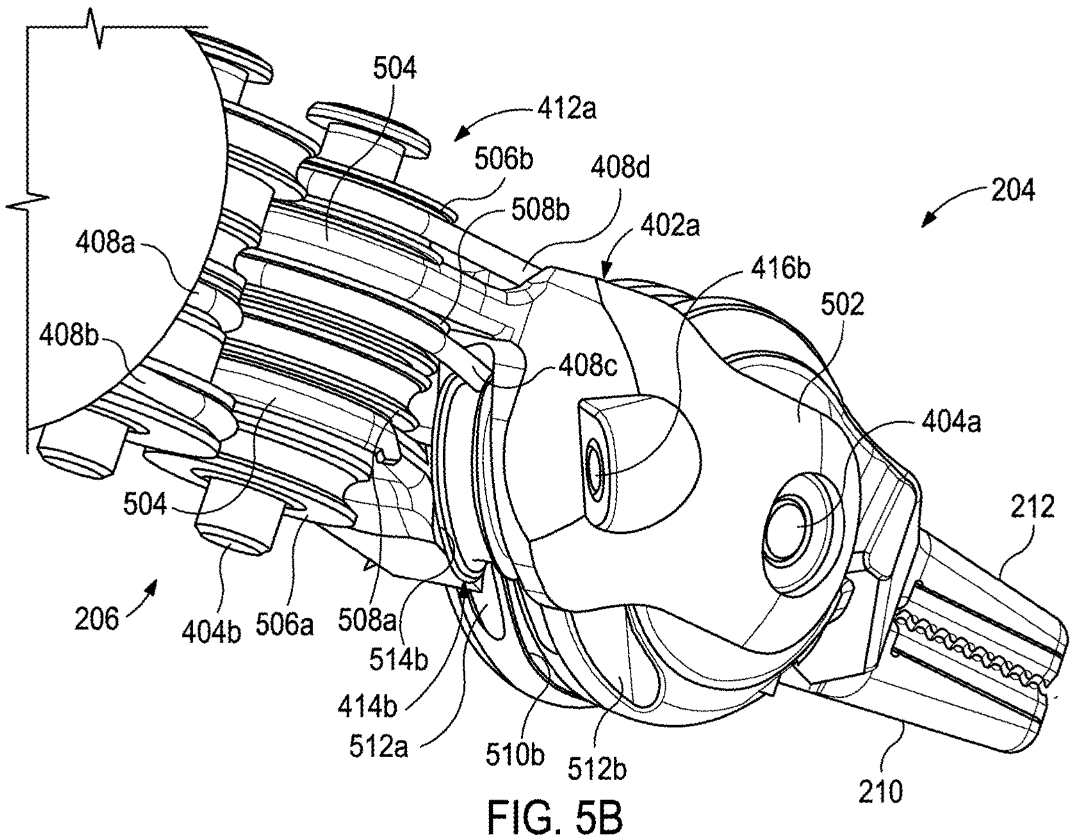

FIGS. 5A and 5B are enlarged isometric views of the end effector 204 and the wrist 206, according to one or more embodiments. More specifically, FIG. 5A is an enlarged, isometric view of the end effector 204 and the wrist 206 from a top right perspective, and FIG. 5B is an enlarged, isometric view of the end effector 204 and the wrist 206 from a bottom left perspective. The proximal clevis 402*b* (FIGS. 4A-4B) is omitted from FIGS. 5A-5B to enable viewing of internal components of the wrist 206.

As illustrated, the distal clevis 402*a* includes first and second distally extending arms 502, and the jaws 210, 212 are arranged between (interpose) the distally extending arms 502 in a gap defined between the arms 502. Each end of the first axle 404*a* extends through or is otherwise mounted to a corresponding one of the distally extending arms 502, and the jaws 210, 212 are rotatably mounted to the first axle 404.

The distal clevis 402*a* further includes first and second proximally extending arms 504 that extend in the opposite direction as the distally extending arms 502. In the illustrated embodiment, the distally extending arms 502 extend in corresponding vertical, parallel planes, and the proximally extending arms 504 extend in corresponding horizontal, parallel planes, where the vertical and horizontal planes are 90° offset from each other.

The first set of pulleys 412*a* is rotatably mounted to the proximally extending arms 504 at the second axle 404*b*, which extends through corresponding apertures (not visible) defined in the proximally extending arms 504. In other embodiments, however, the proximally extending arms 504 may be moved to the center of the device and combined as a single arm. In such embodiments, and depending on where the redirect pulleys 414*a,b* and the proximal pulleys 508*a,b* are placed, a gap would be formed in the distal clevis 402*a* and the single arm can be situated in said gap. As illustrated, the first set of pulleys 412*a* includes first and second outer pulleys 506*a,b* and first and second inner pulleys 508*a,b*. The outer pulleys 506*a,b* are arranged at or near the opposing ends of the second axle 404*b*, and the inner pulleys 508*a,b* interpose the outer pulleys 506*a,b* and, more particularly, are arranged between (interpose) the proximally extending arms 504 in a gap defined between the arms 504. Alternatively, the arms 504 may be defined by the gap between the pulleys 506*a,b*, 508*a,b*. The first and second drive cables 408*a,b* are directed through the wrist 206 on the first outer and inner pulleys 506*a*, 508*a*, respectively, and the third and fourth drive cables 408*c,d* are directed through the wrist 206 on the second outer and inner pulleys 506*b*, 508*b*, respectively. More particularly, the first drive cable 408*a* (i.e., the first closure cable) is routed about the first inner pulley 508*a*, the second drive cable 508*b* (i.e., the first open cable) is routed about the first outer pulley 506*a*, the third drive cable 508*c* (i.e., the second closure cable) is routed about the second inner pulley 508_b_, and the fourth drive cable 508_d_ (i.e., the second open cable) is routed about the second outer pulley 506_b_.

As illustrated, the inner pulleys 508_a,b_ exhibit a larger diameter when compared to the outer pulleys 506_a,b_. Since the inner pulleys 508_a,b_ are configured to route the first and second closure cables 408_a,c_ to the end effector 204, the larger diameter may provide increased mechanical advantage for the closure cables 408_a,c_ while moving the jaws 210, 212 in pitch. Having a larger diameter may also prove advantageous in decreasing the amount of potential bending fatigue that the first and second closure cables 408_a,c_ may experience (undergo) during prolonged operation of the end effector 204. In other embodiments, however, it is contemplated herein that the outer and inner pulleys 506_a,b_, 508_a,b_ exhibit substantially the same diameter, without departing from the scope of the disclosure.

The first drive cable 408_a_ (i.e., the first closure cable) is conveyed from the first inner pulley 508_a_ to the first redirect pulley 414_a_ (FIG. 5A), which redirects the trajectory of the first closure cable 408_a_ to a first closure pulley or "groove" 510_a_ (FIG. 5A) defined in the first jaw 210. Similarly the third drive cable 408_c_ (i.e., the second closure cable) is conveyed from the second inner pulley 508_b_ to the second redirect pulley 414_b_ (FIG. 5B), which redirects the trajectory of the second closure cable 408_c_ to a second closure pulley or "groove" 510_b_ (FIG. 5B) defined in the second jaw 212. Moreover, the second drive cable 408_b_ (i.e., the first open cable) is conveyed from the first outer pulley 506_a_ directly to a first open pulley or "groove" 512_a_ defined in the first jaw 210. Similarly, the fourth drive cable 408_d_ (i.e., the second open cable) is conveyed from the second outer pulley 506_b_ directly to a second open pulley or "groove" 512_b_ (FIG. 5B) defined in the second jaw 212.

In some embodiments, as illustrated, the diameter of the first and second closure grooves 510_a,b_ is greater than the diameter of the first and second open grooves 512_a,b_. Similar to the advantages provided by the larger diameter outer pulleys 506_a,b_, the larger diameter closure grooves 510_a,b_ may prove advantageous in providing an increased mechanical advantage for the closure cables 408_a,c_ during closure of the jaws 210, 212. Moreover, a larger diameter may also prove advantageous in decreasing the amount of potential bending fatigue that the first and second closure cables 408_a,c_ may experience (undergo), thus prolonging the useful life of the closure cables 408_a,c_.

In some embodiments, as illustrated, the distal clevis 402_a_ may provide and otherwise define a first slot 514_a_ (FIG. 5A) configured to accommodate and otherwise receive the first redirect pulley 414_a_. The distal clevis 402_a_ may further provide and otherwise define a second slot 514_b_ (FIG. 5B) configured to accommodate and otherwise receive the second redirect pulley 414_b_. The redirect pulleys 414_a,b_ are rotatably mounted to the corresponding redirect axles 416_a, b_, respectively, which extend laterally through the corresponding slots 514_a,b_, respectively.

The first and second redirect pulleys 414_a,b_ serve to connect two perpendicular planes along a single line. More specifically, the planes through which the first inner pulley 508_a_ and the first closure groove 510_a_ extend are 90° offset, and the first redirect pulley 414_a_ extends in a plane that is angularly offset from each of these planes. As discussed below, this may help eliminate the fleet angle between the first inner pulley 508_a_ and the first closure groove 510_a_, thus directing the first closure cable 408_a_ directly into the trough of the first closure groove 510_a_. Similarly, the planes through which the second inner pulley 508_b_ and the second closure groove 510_b_ extend are 90° offset, and the second redirect pulley 414_b_ extends in a plane that is angularly offset from both of these planes. As also discussed below, this helps eliminate the fleet angle between the second inner pulley 508_b_ the second closure 510_b_, thus directing the second closure cable 408_c_ directly into the trough of the second closure groove 510_b_. The foregoing description is graphically supported in more detail below with reference to FIGS. 7A-7C.

Figure 6:
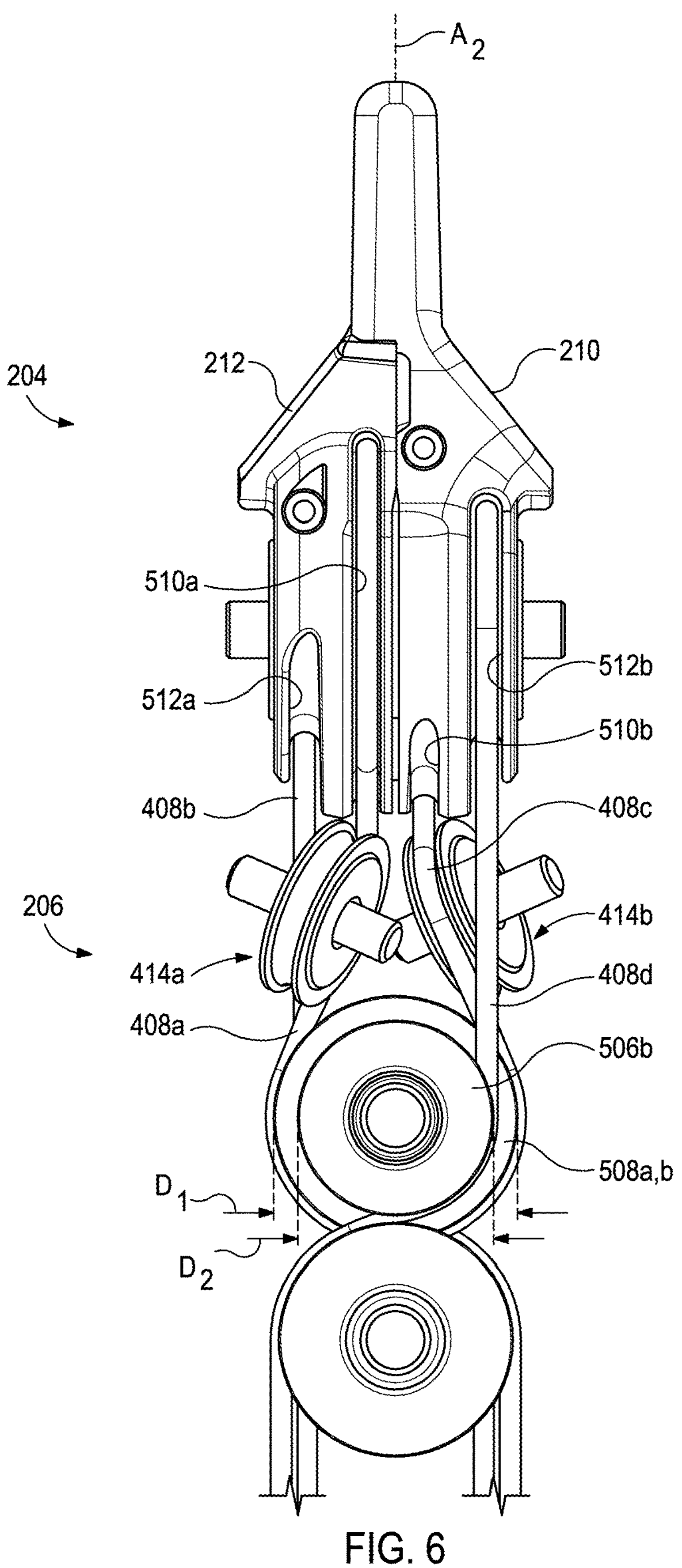
FIG. 6 is a plan or top view of the end effector and the wrist, according to one or more embodiments.

FIG. 6 is an enlarged plan or top view of the end effector 204 and the wrist 206, according to one or more embodiments. In FIG. 6, both the distal and proximal clevises 402_a,b_ (FIGS. 4A-4B) are omitted to enable viewing of the internal components of the wrist 206. As illustrated, the first drive cable 408_a_ (i.e., the first closure cable) is conveyed from the first inner pulley 508_a_ to the first redirect pulley 414_a_, which redirects the trajectory of the first closure cable 408_a_ to the first closure groove 510_a_ defined in the first jaw 210. Similarly, the third drive cable 408_c_ (i.e., the second closure cable) is conveyed from the second inner pulley 508_b_ to the second redirect pulley 414_b_, which redirects the trajectory of the second closure cable 408_c_ to the second closure groove 510_b_ defined in the second jaw 212. Moreover, the second drive cable 408_b_ (i.e., the first open cable) is conveyed from the first outer pulley 506_a_ (not visible in FIG. 6, see FIGS. 5A-5B) directly to the first open groove 512_a_ defined in the first jaw 210. Similarly, the fourth drive cable 408_d_ (i.e., the second open cable) is conveyed from the second outer pulley 506_b_ directly to the second open groove 512_b_ defined in the second jaw 212.

When the end effector 204 is assembled, the first and second closure grooves 510_a,b_ are provided adjacent and otherwise close to the longitudinal axis $A_2$ of the end effector 204. In contrast, the first and second open grooves 512_a,b_ are provided laterally outward from the first and second closure grooves 510_a,b_ and, therefore, further away from the longitudinal axis $A_2$. In at least one embodiment, as illustrated, the inner pulleys 508_a,b_ exhibit a first diameter $D_1$ that is greater than a second diameter $D_2$ exhibited by the outer pulleys 506_a,b_ (only the second outer pulley 506_b_ visible), but the diameters $D_1$, $D_2$ could alternatively be the same, as mentioned above. The smaller second diameter $D_2$ is configured such that the first and second open cables 408_b,d_ are fed directly to the corresponding open grooves 512_a,b_ while exhibiting (presenting) little or no fleet angle between the outer pulleys 506_a,b_ and the open grooves 512_a,b_, respectively.

As used herein, the term "fleet angle" refers to the difference between the angle at which a cable is traveling and a centerline of a destination pulley or groove (trough). In this example, "fleet angle" refers to the angle at which the open cables 408_b,d_ extend between the outer pulleys 506_a,b_ and the open grooves 512_a,b_. An excessive fleet angle can result in considerable abrasive damage to both the open cables 408_b,d_ and the flanges of the outer pulleys 506_a,b_ and the open grooves 512_a,b_, which could considerably reduce the life of the open cables 408_b,d_ as well as the outer pulleys 506_a,b_ and the open grooves 512_a,b_. Another risk of excessive fleet angle is that the open cables 408_b,d_ could potentially be pulled out of a groove or pulley, alternately referred to as "derailment."

Because of the larger diameter $D_1$ exhibited by the inner pulleys 508_a,b_, if the wrist 206 did not include the redirect pulleys 414_a,b_, the closure cables 408_a,c_ would exhibit (present) a significant fleet angle extending between the inner pulleys 508_a,b_ and the corresponding closure grooves 510_a,b_. Inclusion of the redirect pulleys 414_a,b_, however, significantly reduces or entirely eliminates such fleet angle between the inner pulleys 408*a,b* and the closure grooves 510*a,b*, respectively. More specifically, the redirect pulleys 414*a,b* are arranged and otherwise oriented to receive the closure cables 408*a,c* from the inner pulleys 508*a,b*, respectively, such that the closure cables 408*a,c* exhibit little or no fleet angle between the inner pulleys 508*a,b* and the redirect pulleys 414*a,b*. Furthermore, the redirect pulleys 414*a,b* are further arranged and otherwise oriented to redirect the closure cables 408*a,c* to the closure grooves 510*a,b* such that the closure cables 408*a,c* exhibit little or no fleet angle between the redirect pulleys 414*a,b* and the closure grooves 510*a,b*, thus reducing the risk of derailment, as graphically depicted in FIGS. 7A-7C below.

With continued reference to FIG. 6, FIGS. 7A-7C schematically depict how the inclusion of a redirect pulley between yaw and pitch pulleys can eliminate fleet angle, according to the principles of the present disclosure. As illustrated, portions of a closure cable 702 are wrapped partially around a yaw pulley 704 and a pitch pulley 706. The closure cable 702 may represent either closure cable 408*a,c*, the yaw pulley 704 may represent either inner pulley 508*a,b*, and the pitch pulley 706 may represent either closure groove 510*a,b* defined in either jaw 210, 212, respectively. The pitch pulley 706 is rotatably mounted to the first axle 404*a* and extends along the first pivot axis $P_1$, and the yaw pulley 704 is rotatably mounted to the second axle 404*b* and extends along the second pivot axis $P_2$. As mentioned above, the first and second pivot axes $P_1$, $P_2$ are substantially perpendicular (orthogonal) to each other.

To increase the mechanical advantage of the wrist 206, the size of the pitch pulley 706 may be increased relative to and otherwise larger than the size of the yaw pulley 704. Moreover, to fit the larger pitch pulley 706 within the shaft outline, the pitch pulley 706 may be moved towards a center plane of the wrist 206. This changes the pathway for the closure cable 702 in a manner that could potentially create a significant amount of cable fleet, which could force the closure cable 702 to contact edges of the pulleys 704, 706 and thereby result in accelerated cable wear and failure.

According to embodiments of this disclosure, a redirect pulley 708 (FIG. 7C) may be used to reduce or entirely eliminate the fleet angle of the closure cable 702 extending between the yaw and pitch pulleys 704, 706. The redirect pulley 708 may represent either redirect pulley 414*a,b* described herein. The redirect pulley 708 may be located in a plane that contains straight segments of the closure cable 702 intersecting in a point and extending tangentially from both the yaw and pitch pulleys 704, 706. In particular, the distance between the yaw and pitch pulleys 704, 706 may be increased, and the pathway of each segment of the closure cable 702 may be routed tangent (i.e., no fleet) from the yaw and pitch pulleys 704, 706 until the cable segments intersect at a point X. The straight section of each intersecting segment of the closure cable 702 belongs to a single plane that is used to locate the redirect pulley 708. This results in a pulley and cable arrangement for the wrist 206 that incorporates maximized pitch pulley 706 with no fleet on the closure cable 702. Moreover, as described above, this results in placement of the redirect pulley 708 such that the closure cable 702 extends diametrically tangent from the redirect pulley 708 to both the yaw and pitch pulleys 704, 706. This helps reduce or entirely eliminate the fleet angle of the closure cable 702 as it is received at the pitch pulley 706.

Embodiments disclosed herein include:

A. A surgical tool includes a drive housing having an elongate shaft extending therefrom, an end effector arranged at a distal end of the shaft and including opposing first and second jaws, and a wrist interposing the shaft and the end effector and including a distal clevis to which the first and second jaws are rotatably mounted at a first axle, a proximal clevis rotatably mounted to the distal clevis at a second axle and operatively coupled to the distal end of the shaft, a set of pulleys rotatably mounted to the second axle, and first and second redirect pulleys rotatably mounted to the distal clevis and axially interposing the set of pulleys and the first and second jaws. The surgical tool further includes a first closure cable extending from the drive housing and through the set of pulleys to the first redirect pulley, which redirects the first closure cable with no fleet angle to a first closure groove provided in the first jaw, and a second closure cable extending from the drive housing and through the set of pulleys to the second redirect pulley, which redirects the second closure cable with no fleet angle to a second closure groove provided in the second jaw.

B. An end effector for a surgical tool includes opposing first and second jaws rotatably mounted to a distal clevis at a first axle, a proximal clevis rotatably mounted to the distal clevis at a second axle, a set of pulleys rotatably mounted to the second axle, first and second redirect pulleys rotatably mounted to the distal clevis and axially interposing the set of pulleys and the first and second jaws, a first closure cable extendable through the set of pulleys to the first redirect pulley, which redirects the first closure cable with no fleet angle to a first closure groove provided in the first jaw, and a second closure cable extendable through the set of pulleys to the second redirect pulley, which redirects the second closure cable with no fleet angle to a second closure groove provided in the second jaw.

C. A method of operating a surgical tool includes bringing the surgical tool in proximity of a patient, the surgical tool including a drive housing having an elongate shaft extending therefrom, an end effector arranged at a distal end of the shaft and including opposing first and second jaws, and a wrist interposing the shaft and the end effector and including a distal clevis to which the first and second jaws are rotatably mounted at a first axle, a proximal clevis rotatably mounted to the distal clevis at a second axle and operatively coupled to the distal end of the shaft, a set of pulleys rotatably mounted to the second axle, and first and second redirect pulleys rotatably mounted to the distal clevis and axially interposing the set of pulleys and the first and second jaws. The method further including actuating a first closure cable extending from the drive housing and through the set of pulleys to the first redirect pulley, which redirects the first closure cable with no fleet angle to a first closure groove provided in the first jaw, and actuating a second closure cable extending from the drive housing and through the set of pulleys to the second redirect pulley, which redirects the second closure cable with no fleet angle to a second closure groove provided in the second jaw.

Each of embodiments A, B, and C may have one or more of the following additional elements in any combination: Element 1: wherein the set of pulleys comprises a first set of pulleys, the wrist further including a second set of pulleys rotatably mounted to the proximal clevis at a third axle and located proximal from the second axle. Element 2: wherein the first redirect pulley is rotatably mounted to the distal clevis at a first redirect axle, and the second redirect pulley is rotatably mounted to the distal clevis at a second redirect axle. Element 3: wherein a first pivot axis extends through the first axle and a second pivot axis extends through the second axle and is perpendicular to the first pivot axis, and wherein a first redirect axis extends through the first redirect axle and a second redirect axis extends through the second redirect axle, the first and second redirect axes being angularly offset from both the first and second pivot axes. Element 4: further comprising first and second open cables, wherein the set of pulleys includes first and second outer pulleys arranged at or near opposing ends of the second axle, the first and second open cables being directed through the wrist on the first and second outer pulleys, respectively, and first and second inner pulleys interposing the first and second outer pulleys, the closure cables being directed through the wrist on the first and second inner pulleys, respectively, wherein a diameter of the first and second inner pulleys is larger than a diameter of the first and second outer pulleys. Element 5: wherein the first closure and open cables terminate at the first jaw and are configured for antagonistic operation, and wherein the second closure and open cables terminate at the second jaw and are configured for antagonistic operation. Element 6: wherein the first and second outer pulleys convey the first and second open cables to first and second open grooves defined in the first and second jaws, respectively, with no fleet angle. Element 7: wherein the first and second redirect pulleys are arranged such that the first and second closure cables are directed to the first and second redirect pulleys from the first and second inner pulleys with no fleet angle.

Element 8: wherein the first redirect pulley is rotatably mounted to the distal clevis at a first redirect axle, and the second redirect pulley is rotatably mounted to the distal clevis at a second redirect axle, wherein a first pivot axis extends through the first axle and a second pivot axis extends through the second axle and is perpendicular to the first pivot axis, and wherein a first redirect axis extends through the first redirect axle and a second redirect axis extends through the second redirect axle, the first and second redirect axes being angularly offset from both the first and second pivot axes. Element 9: further comprising first and second open cables, wherein the set of pulleys includes first and second outer pulleys arranged at or near opposing ends of the second axle, the first and second open cables being directed through the wrist on the first and second outer pulleys, respectively, and first and second inner pulleys interposing the first and second outer pulleys, the closure cables being directed through the wrist on the first and second inner pulleys, respectively, wherein a diameter of the first and second inner pulleys is larger than a diameter of the first and second outer pulleys. Element 10: wherein the first closure and open cables terminate at the first jaw and are configured for antagonistic operation, and wherein the second closure and open cables terminate at the second jaw and are configured for antagonistic operation. Element 11: wherein the first and second outer pulleys convey the first and second open cables to first and second open grooves defined in the first and second jaws, respectively, with no fleet angle. Element 12: wherein a diameter of the first and second closure grooves is greater than a diameter of the first and second open grooves. Element 13: wherein the first and second redirect pulleys are arranged such that the first and second closure cables are directed to the first and second redirect pulleys from the first and second inner pulleys with no fleet angle. Element 14: wherein the first inner pulley extends through a first plane and the first closure groove extends through a second plane 90° offset from the first plane, the first redirect pulley extending in a plane angularly offset from the first and second planes, and wherein the second inner pulley extends through a third plane and the second closure groove extends through a fourth plane 90° offset from the third plane, the second redirect pulley extending in a plane angularly offset from the third and fourth planes. Element 15: wherein the distal clevis defines a first slot aligned with the first plane and configured to accommodate and receive the first redirect pulley, and further defines a second slot aligned with the third plane and configured to accommodate and receive the second redirect pulley, the first and second redirect axles extending laterally through the first and second slots, respectively.

Element 16: further comprising actuating the first closure cable antagonistically with a first open cable, the first closure and open cables terminating at the first jaw, and actuating the second closure cable antagonistically with a second open cable, the second closure and open cables terminating at the second jaw, wherein the set of pulleys includes first and second outer pulleys arranged at or near opposing ends of the second axle, the first and second open cables being directed through the wrist on the first and second outer pulleys, respectively, and first and second inner pulleys interposing the first and second outer pulleys, the closure cables being directed through the wrist on the first and second inner pulleys, respectively, wherein a diameter of the first and second inner pulleys is larger than a diameter of the first and second outer pulleys. Element 17: further comprising conveying the first open cable from the first outer pulley to the first open groove with no fleet angle, and conveying the second open cable from the second outer pulley to the second open groove with no fleet angle.

By way of non-limiting example, exemplary combinations applicable to A, B, and C include: Element 2 with Element 3; Element 4 with Element 5; Element 4 with Element 6; Element 4 with Element 7; Element 9 with Element 10; Element 9 with Element 11; Element 11 with Element 12; Element 9 with Element 13; Element 9 with Element 14; Element 14 with Element 15; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a"

or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure.

What is claimed is the following:

1. A surgical tool, comprising:

a drive housing having an elongate shaft extending therefrom;

an end effector arranged at a distal end of the shaft and including opposing first and second jaws;

a wrist interposing the shaft and the end effector and including:

a distal clevis to which the first and second jaws are rotatably mounted at a first axle;

a proximal clevis rotatably mounted to the distal clevis at a second axle and operatively coupled to the distal end of the shaft;

a set of pulleys rotatably mounted to the second axle; and first and second redirect pulleys rotatably mounted to the distal clevis and axially interposing the set of pulleys and the first and second jaws;

a first closure cable extending from the drive housing and through the set of pulleys to the first redirect pulley, which redirects the first closure cable with no fleet angle to a first closure groove provided in the first jaw; and a second closure cable extending from the drive housing and through the set of pulleys to the second redirect pulley, which redirects the second closure cable with no fleet angle to a second closure groove provided in the second jaw, wherein the distal clevis includes:

opposing first walls that define a first slot for receiving the first redirect pulley; and opposing second walls that define a second slot for receiving the second redirect pulley.

2. The surgical tool of claim 1, wherein the set of pulleys comprises a first set of pulleys, the wrist further including a second set of pulleys rotatably mounted to the proximal clevis at a third axle and located proximal from the second axle.

3. The surgical tool of claim 1, wherein the first redirect pulley is rotatably mounted to the distal clevis at a first redirect axle, and the second redirect pulley is rotatably mounted to the distal clevis at a second redirect axle.

4. The surgical tool of claim 3, wherein a first pivot axis extends through the first axle and a second pivot axis extends through the second axle and is perpendicular to the first pivot axis, and wherein a first redirect axis extends through the first redirect axle and a second redirect axis extends through the second redirect axle, the first and second redirect axes being angularly offset from both the first and second pivot axes.

5. The surgical tool of claim 1, further comprising first and second open cables, wherein the set of pulleys includes:

first and second outer pulleys arranged at or near opposing ends of the second axle, the first and second open cables being directed through the wrist on the first and second outer pulleys, respectively; and first and second inner pulleys interposing the first and second outer pulleys, the closure cables being directed through the wrist on the first and second inner pulleys, respectively, wherein a diameter of the first and second inner pulleys is larger than a diameter of the first and second outer pulleys.

6. The surgical tool of claim 5, wherein the first and second outer pulleys convey the first and second open cables to first and second open grooves defined in the first and second jaws, respectively, with no fleet angle.

7. The surgical tool of claim 5, wherein the first and second redirect pulleys are arranged such that the first and second closure cables are directed to the first and second redirect pulleys from the first and second inner pulleys with no fleet angle.

8. An end effector for a surgical tool, comprising:

opposing first and second jaws rotatably mounted to a distal clevis at a first axle;

a proximal clevis rotatably mounted to the distal clevis at a second axle;

a set of pulleys rotatably mounted to the second axle;

first and second redirect pulleys rotatably mounted to the distal clevis and axially interposing the set of pulleys and the first and second jaws;

a first closure cable extendable through the set of pulleys to the first redirect pulley, which redirects the first closure cable with no fleet angle to a first closure groove provided in the first jaw; and a second closure cable extendable through the set of pulleys to the second redirect pulley, which redirects the second closure cable with no fleet angle to a second closure groove provided in the second jaw, wherein the distal clevis includes:

opposing first walls that define a first slot for receiving the first redirect pulley; and opposing second walls that define a second slot for receiving the second redirect pulley.

9. The end effector of claim 8, wherein the first redirect pulley is rotatably mounted to the distal clevis at a first redirect axle, and the second redirect pulley is rotatably mounted to the distal clevis at a second redirect axle, wherein a first pivot axis extends through the first axle and a second pivot axis extends through the second axle and is perpendicular to the first pivot axis, and wherein a first redirect axis extends through the first redirect axle and a second redirect axis extends through the second redirect axle, the first and second redirect axes being angularly offset from both the first and second pivot axes.

10. The end effector of claim 8, further comprising first and second open cables, wherein the set of pulleys includes:

first and second outer pulleys arranged at or near opposing ends of the second axle, the first and second open cables being directed through the wrist on the first and second outer pulleys, respectively; and first and second inner pulleys interposing the first and second outer pulleys, the closure cables being directed through the wrist on the first and second inner pulleys, respectively, wherein a diameter of the first and second inner pulleys is larger than a diameter of the first and second outer pulleys.

11. The end effector of claim 10, wherein the first closure and open cables terminate at the first jaw and are configured for antagonistic operation, and wherein the second closure and open cables terminate at the second jaw and are configured for antagonistic operation.

12. The end effector of claim 10, wherein the first and second outer pulleys convey the first and second open cables to first and second open grooves defined in the first and second jaws, respectively, with no fleet angle.

13. The end effector of claim 12, wherein a diameter of the first and second closure grooves is greater than a diameter of the first and second open grooves.

14. The end effector of claim 10, wherein the first and second redirect pulleys are arranged such that the first and second closure cables are directed to the first and second redirect pulleys from the first and second inner pulleys with no fleet angle.

15. The end effector of claim 10, wherein the first inner pulley extends through a first plane and the first closure groove extends through a second plane 90° offset from the first plane, the first redirect pulley extending in a plane angularly offset from the first and second planes, and wherein the second inner pulley extends through a third plane and the second closure groove extends through a fourth plane 90° offset from the third plane, the second redirect pulley extending in a plane angularly offset from the third and fourth planes.

16. The end effector of claim 15, wherein the distal clevis defines a first slot aligned with the first plane and configured to accommodate and receive the first redirect pulley, and further defines a second slot aligned with the third plane and configured to accommodate and receive the second redirect pulley, the first and second redirect axles extending laterally through the first and second slots, respectively.

17. A method of operating a surgical tool that includes:

a drive housing having an elongate shaft extending therefrom;

an end effector arranged at a distal end of the shaft and including opposing first and second jaws; and a wrist interposing the shaft and the end effector and including a distal clevis to which the first and second jaws are rotatably mounted at a first axle, a proximal clevis rotatably mounted to the distal clevis at a second axle and operatively coupled to the distal end of the shaft, a set of pulleys rotatably mounted to the second axle, and first and second redirect pulleys rotatably mounted to the distal clevis and axially interposing the set of pulleys and the first and second jaws, wherein the distal clevis includes opposing first walls that define a first slot for receiving the first redirect pulley opposing second walls that define a second slot for receiving the second redirect pulley, wherein the method comprises:

actuating a first closure cable extending from the drive housing and through the set of pulleys to the first redirect pulley, which redirects the first closure cable with no fleet angle to a first closure groove provided in the first jaw; and actuating a second closure cable extending from the drive housing and through the set of pulleys to the second redirect pulley, which redirects the second closure cable with no fleet angle to a second closure groove provided in the second jaw.

18. The method of claim 17, further comprising:

actuating the first closure cable antagonistically with a first open cable, the first closure and open cables terminating at the first jaw; and actuating the second closure cable antagonistically with a second open cable, the second closure and open cables terminating at the second jaw, wherein the set of pulleys includes:

first and second outer pulleys arranged at or near opposing ends of the second axle, the first and second open cables being directed through the wrist on the first and second outer pulleys, respectively; and first and second inner pulleys interposing the first and second outer pulleys, the closure cables being directed through the wrist on the first and second inner pulleys, respectively, wherein a diameter of the first and second inner pulleys is larger than a diameter of the first and second outer pulleys.

19. The method of claim 18, further comprising:

conveying the first open cable from the first outer pulley to the first open groove with no fleet angle; and conveying the second open cable from the second outer pulley to the second open groove with no fleet angle.

* * * * *